United States Patent
Roberts et al.

(12)

(10) Patent No.: US 6,228,955 B1
(45) Date of Patent: May 8, 2001

(54) ASYMMETRIC EPOXIDES, THEIR SYNTHESIS AND USE

(75) Inventors: Stanley Michael Roberts, Liverpool; Brian Michael Adger, Cambridge, both of (GB)

(73) Assignee: Chirotech Technology, Ltd. (GB)

( * ) Notice: Subject to any disclaimer, the term of this patent is extended or adjusted under 35 U.S.C. 154(b) by 0 days.

(21) Appl. No.: 08/953,946

(22) Filed: Oct. 20, 1997

Related U.S. Application Data

(63) Continuation-in-part of application No. PCT/GB96/00953, filed on Apr. 19, 1996.

(51) Int. Cl.[7] .................................................. C08F 283/04

(52) U.S. Cl. ........................ 525/426; 549/525; 549/530; 549/539; 549/549

(58) Field of Search ........................... 523/461; 549/525, 549/530, 539, 549; 525/426

(56) References Cited

U.S. PATENT DOCUMENTS 5,110,959 * 5/1992 Flisher et al. ......................... 549/513

FOREIGN PATENT DOCUMENTS

| | | |
|---|---|---|
| 0336841 | 10/1989 | (EP) . |
| 9113066 | 9/1991 | (WO) . |

OTHER PUBLICATIONS

Banfi, S. et al. (1984) "Asymmetric Epoxidation of Electron–Poor Olefins—V[1]: Influence on Stereoselectivity of the Structure of Poly–α–Aminoacids Used as Catalysts" *Tetrahedron* vol. 40, No. 24, pp. 5207–5211.

Baures, P. et al. (1990) "An Efficient Asymmetric Synthesis of Substituted Phenyl Glycidic Esters" *Tetrahedron Lett.* vol. 31, No. 45, pp. 6501–6504.

Boa, A.N., P.R. Jenkins, N.J. Lawrence (1994) "Recent Progress in the Synthesis of Taxanes" *Contemporary Organic Synthesis* 1:47–75.

Colonna, S. et al. (1983) "Synthetic Enzymes—4[1]: Highly Enantioselective Epoxidation by Means of Polyaminoacids in a Triphase System: Influence of Structural Variations Within the Catalysts" *Tetrahedron* vol. 39, No. 9, pp. 1635–1641.

Corey, E.J. and S. Choi (1991) "Highly Enantioselective Routes to Darzens and Acetate Aldol Products from Achiral Aldehydes and t–Butyl Bromoacetate" *Tetrahedron Lett.* vol. 32, No. 25, pp. 2857–2860.

Gao, Y. et al. (1987) "Catalytic Asymmetric Epoxidation and Kinetic Resolution: Modified Procedures Including in Situ Derivatization" *J. Am. Chem. Soc.* 109:5765–5780.

Itsuno, S., M. Sakakura, K. Ito (1990) "Polymer–Supported Poly(amino acids) as New Asymmetric Epoxidation Catalyst of α, β–Unsaturated Ketones" *J. Org. Chem.* 55:6047–6049.

Jacobsen, E. (1993) "Chapter 4.2 in Catalytic Asymmetric Synthesis: Asymmetric Catalytic Epoxidation of Unfunctionalized Olefins" Ed. I. Ojima, VCH, New York, pp. 159–202.

Juliá, S., J. Masana, J. Vega (1980) "Synthetic Enzymes'. Highly Stereoselective Epoxidation of Chalcone in a Triphasic Toluene–Water–Poly[(S)–alanine] System" *Angew. Chem. Int. Ed. Engl.* 19:929–931.

Juliá, S. et al. (1982) "Synthetic Enzymes. Part 2. Catalytic Asymmetric Epoxidation by means of Polyamino–acids in a Triphase System" *J. Chem. Soc. Perkin Trans. I*, 1317–1324.

Katsuki, T. et al. (1980) "The First Practical Method for Asymmetric Epoxidation" *J. Am. Chem. Soc.* vol. 102, No. 18, 5974–5976.

Lin, J.T. et al. (1989) "Stereoselective Synthesis of Chiral 2,3–Epoxycompounds Possessing Fluorinated Methyl Groups" *J. Flourine Chem.* 44:113–120.

Matano, Yoshihiro (1994) "Triphenylbismuthonium 2–Oxoalkylide, A Moderately Stabilized Bismuthonium Ylide: Generation and Reactions with Some Electrophiles" *J. Chem. Soc. Perkin Trans. I*, 2703–2709.

Meth–Cohn, O., R.M. Horak, G. Fouch'' (1994) "Baker's Yeast–mediated Transformations of α–Keto Epoxides" *J. Chem. Soc. Perkin Trans. I*, 1517–1527.

Wang, Z.–M. H.C. Kolb, K.B. Sharpless (1994) "Large–Scale and Highly Enantioselective Synthesis of the Taxol C–13 Side Chain through Asymmetric Dihydroxylation" *J. Org. Chem.* 59:5104–5105.

Denis, Jean–Noël, Arlene Correa, Andrew E. Greene (1990) "An Improved Synthesis of the Taxol Side Chain and of RP 56976" Journal of Organic Chemistry 55:1957–1959.

Treves, Gino R., Hugo Stange, R.A. Olofson (1967) (The Base–Induced Rearrangements of α–Epoxy Ketones Journal of American Chemical Society 89(24):6257–6260.

Li, Deng, Eric N. Jacobsen (1992) "A Practical, Highly Enantioselective Synthesis of the Taxol Side Chain via Asymmetric Catalysis" Journal of Organic Chemistry 57:4320–4323.

Abstract EP 0 336 841 By Derwent Info., 1998.

* cited by examiner

*Primary Examiner*—Robert Dawson
*Assistant Examiner*—D. Aylward
(74) *Attorney, Agent, or Firm*—Saliwanchik, Lloyd & Saliwanchik

(57) ABSTRACT

A process for preparing an optically-enriched chiral epoxide of formula I (I)

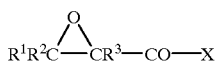

wherein $R^1$, $R^2$ and $R^3$ are each independently selected from H, R, R—CO— and R—O—CO—, each R independently being substantially a hydrocarbon group of up to 20 carbon atoms, and X is an alkyl or cycloalkyl group of up to 10 carbon atoms, provided that —CO—X is not enolisable, which comprises the asymmetric epoxidation of a corresponding prochiral alkene of formula II $$R^1R^2C\!\!=\!\!CR^3\text{---}CO\text{---}X \qquad (II)$$

by reaction with an oxidant in the presence of a chiral catalyst. Many optically-enriched epoxides (I) are novel.

25 Claims, 3 Drawing Sheets

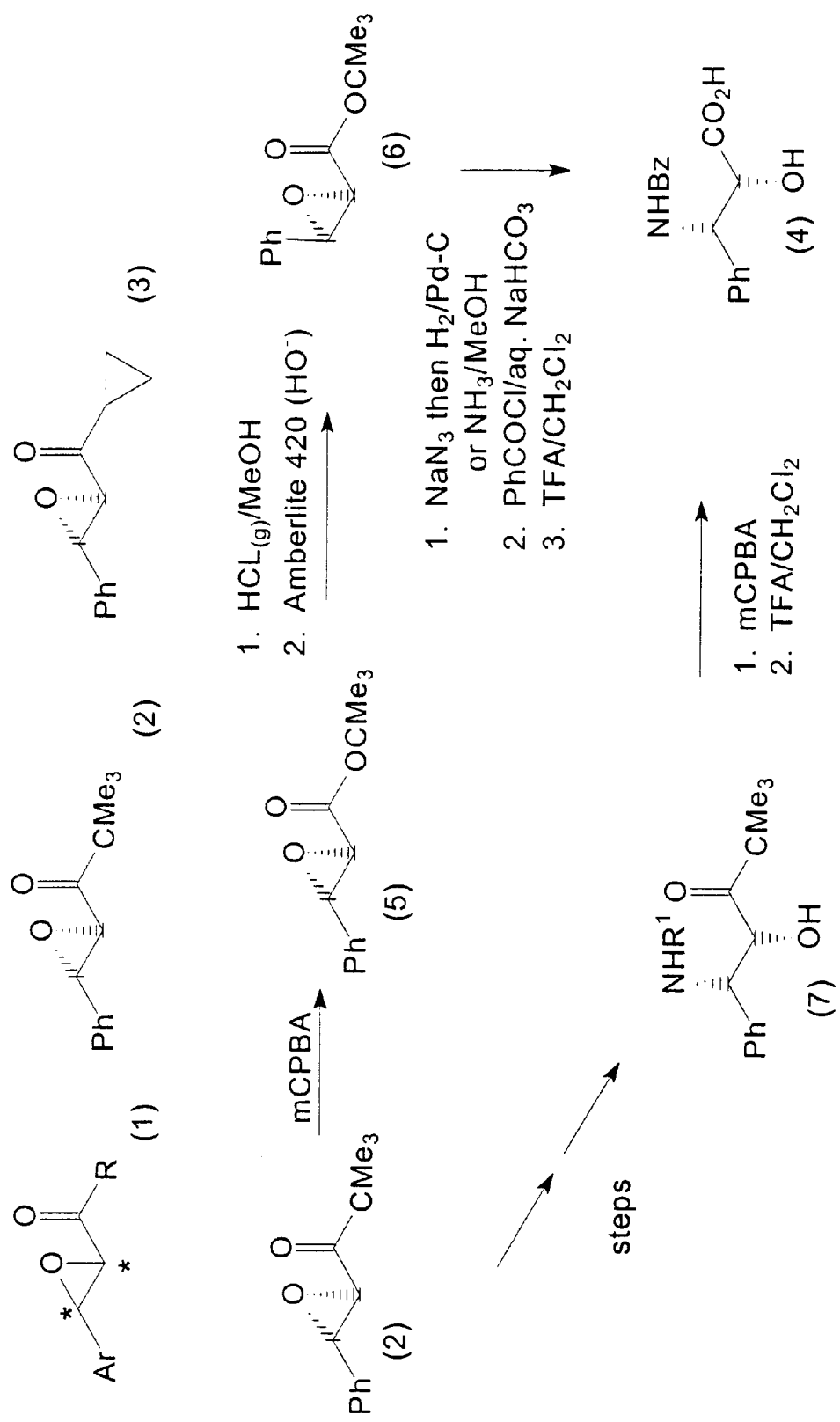
SCHEME 1

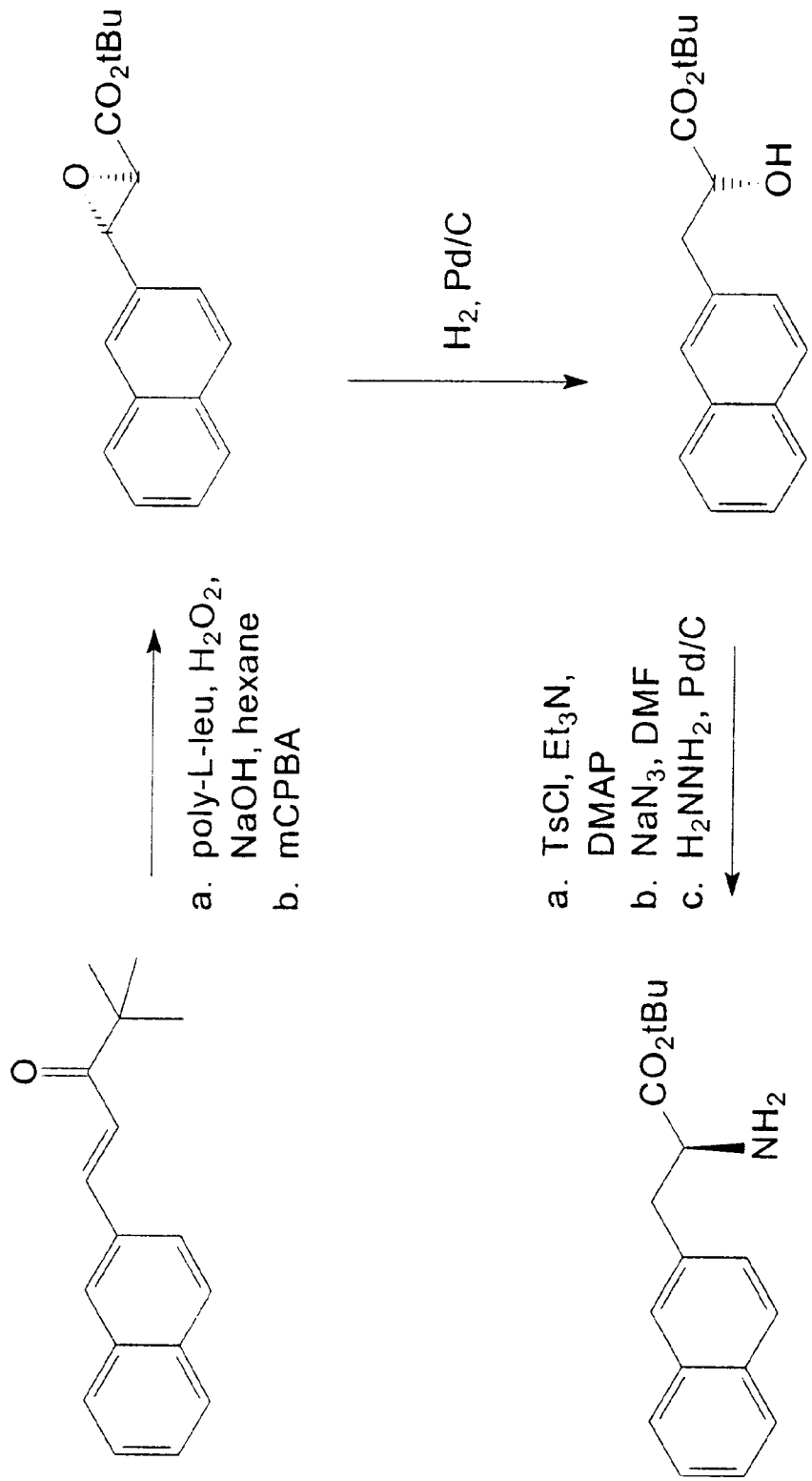
SCHEME 2

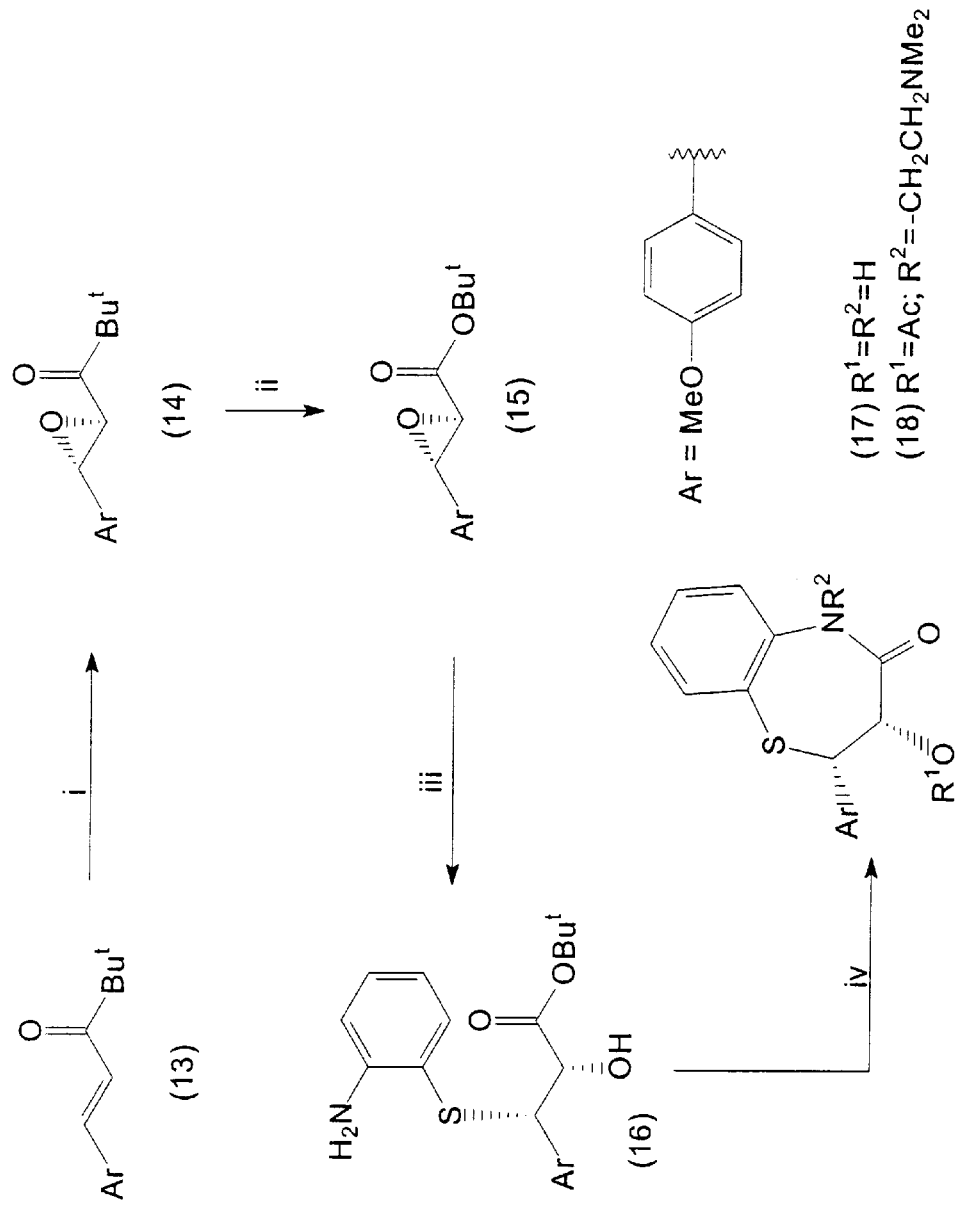
SCHEME 3

ASYMMETRIC EPOXIDES, THEIR SYNTHESIS AND USE

RELATION TO EARLIER APPLICATION

This Application is a continuation-in-part of International Patent Application No. PCT/GB96/00953, filed Apr. 19, 1996.

FIELD OF THE INVENTION

This invention relates to epoxides, their synthesis by the asymmetric epoxidation of enones, and their use.

BACKGROUND OF THE INVENTION

The enantioselective epoxidation of prochiral alkenes is a valuable methodology, which enables two stereogenic centres to be created in a single synthetic operation. Established methods tend to be limited to specific classes of substrate. The best known is the titanium tartrate-catalysed epoxidation of allylic alcohols, which was first reported by Sharpless as a stoichiometric method, in Katsuki et al, J. Am. Chem. Soc. (190) 102:5974, and later adapted into a catalytic variant; see Gao et al, J. Am. Chem. Soc (1987) 109:5765.

More recently, epoxidations employing chiral (salen)Mn (III) catalysts have been applied to a variety of alkene substrates, both unfunctionalised and functionalised; see Jacobsen, Chapter 4.2 in Catalytic Asymmetric synthesis, ed. I. Ojima (1993) VCH, New York.

Although both these known processes are proven as generic methodologies for laboratory-scale synthesis, reliance on metal-based catalysts and reagents means that operation on a large scale can be disadvantageous in terms of cost, work-up procedure and effluent disposal.

A third and potentially more economical methodology is the use of metal-free synthetic polypeptides such as poly-L-leucine as catalysts for the asymmetric epoxidation of prochiral α,β-unsaturated ketones of the general formula

$R^1R^2C=CR^3—CO—X$ (II)

to give the corresponding optically-enriched epoxides (I)

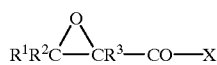

This process was first reported by Julia et al, Angew. Chem. Int. Ed. Engl. (1980) 19:929. However, it is reported that high enantioselectivities are confined to trans-chalcone derivatives; see Juliá et al, J. Chem. Soc., Perkin Trans. 1 (1982) 1317; Colonna et al, Tetrahedron (1983) 39:1635; Banfi et al, Tetrahedron (1984) 40:5297; Baures et al, Tetrahedron Lett. (1990) 31;6501; and Itsuno et al, J. org. Chem. (1990) 55:5047, Thus, this reaction has been considered to be of restricted scope in organic synthesis.

Optically-enriched epoxides are especially suited to nucleophilic ring-opening reactions to give, in stereocontrolled fashion, products bearing heteroatom functionality on adjacent chiral centres. In this respect, (2R,3S)-syn-3-phenylisoserine synthons are reported by Boa et al, Contemporary Organic Synthesis (1994) 1:47, and references therein. Several methods proceed via trans- or cis-phenylglycidate intermediates, prepared by enantioselective oxidation (epoxidation and dihydroxylation) of styrene derivatives; see Greene, J. Org. Chem. (1990) 55:1957; Jacobsen, J. Org. Chem. (1992) 57:4320; and Sharpless, J. Org. Chem. (1994) 59:5105. Although this is an effective overall strategy, provision of enantiopure phenylglycidates relies on the metal-based epoxidation methodologies described above, and aspects of the downstream chemistry are not well suited to operation on a large scale.

Compounds of formula I are known in racemic form. For example, compounds wherein $R^1$ is phenyl, $R^2$ and $R^3$ are each H, and X is t-butyl or cyclopropyl, are disclosed in EP-A-0336841 and WO-A-0113066, and by Matano, J. Chem. Soc. Perkin Trans. I (1994) 2703, Meth-Cohn, ib. 1517, and Treves, JACS (1967) 89:6257. The nature of the functional groups makes such compounds difficult to separate into constituent enantiomers, by conventional resolution techniques.

An optically-enriched epoxide of formula I ($R^1=CF_3$, $R^2=R^3=H$, X=t-butyl) is reported by Lin et al, J. Fluorine Chem. (1989) 44:113–120. Its synthesis is from optically-enriched 1,1,1-trifluoro-2-hydroxy-5,5-dimathylhexan-4-one, using lithium diisopropylamide. This is not a commercial process.

Corey et al, Tetrahedron Lett. (1991) 32:2857, report the t-butyl glycidate 5 (see Scheme 1) as the product of a chiral Darzens reaction between t-butyl bromoacetate and benzaldehyde.

SUMMARY OF THE INVENTION

It has surprisingly been discovered that asymmetric epoxidation of the type reported by Juliá at al can tolerate a greater range of substituents than is indicated by the prior art. More particularly, the present invention enables the preparation of novel optically-enriched epoxides of formula I wherein $R^1$, $R^2$ and $R^3$ are each independently selected from H, R, R—CO— and R—O—CO—, each R independently being substantially a hydrocarbon group of up to 20 carbon atoms, and X is an alkyl or cycloalkyl group of up to 10 carbon atoms, provided that —CO—X is not enolisable. Novel epoxides of formula I constitute a further aspect of the invention.

BRIEF DESCRIPTION OF THE DRAWINGS

Scheme 1-Synthesis of taxol side-chain synthons
Scheme 2-Synthesis of L-2-naphthylalanine
Scheme 3-Synthesis of Diltiazem

DESCRIPTION OF THE INVENTION

The nature of each of $R^1$, $R^2$ and $R^3$ is not critical, providing that it does not interfere with the asymmetric epoxidation reaction. For example, $R^1$ is essentially a spectator to the reaction, for which the non-enolisable nature of —CO—X is important. $R^1$ may be, for example, a group of up to 10 carbon atoms. $R^2$ and $R^3$, and optionally also $R^1$, may be H. $R^2$ and $R^3$ may be linked, e.g. together are —$(CH_2)_4$—. Any group other than H may comprise C and H atoms only, or may comprise one or more heteroatoms and/or substituents. One preference for $R^1$ is aryl or heteroaryl, optionally linked via a conjugating group to $CR^2$, e.g. phenyl (or substituted phenyl).

Most preferably, X is tert-alkyl, e.g. t-butyl (for example when $R^1$ is phenyl and $R^2$ and $R^3$ are each H), since the substrates for epoxidation are readily available, or simply obtainable from inexpensive readily-available starting materials such as pinacolone. Another simple non-enolisable group is provided when X is cyclopropyl.

X as alkyl can readily be converted to alkoxy by the Baeyer-Villiger reaction. As indicated below, compounds in which X is t-butoxy are of particular interest.

The present invention provides, for example, an asymmetric route to α,β-unsaturated esters or other carboxylates such as amides. This allows access to, for instance, the phenylisoserine component of the anticancer natural product taxol, or provides intermediates for the antihypertensive drug diltiazem (for which purpose $R^1$ is 4-methoxyphenyl; see Scheme 3, below).

Obviously, a benefit of the methodology is that either enantiomer of the epoxide can be obtained with equal facility by using the appropriate catalyst, e.g. either the L- or the D-polyamino-acid. Other catalysts can be used, as may be found effective, by trial and error. The catalyst may be a material obtainable by nucleophile-promoted oligomerisation of an amino-acid carboxy anhydride. An alternative catalyst is the immobilised catalyst system described by Itsonu et al, J. Org. Chem. (1990).

The conditions reported by Juliáet al, supra, for the asymmetric epoxidation comprise a three-phase system of poly-amino-acid catalyst, an organic solvent such as n-hexane, and an aqueous phase containing a large excess of both oxidant (hydrogen peroxide) and alkali (sodium hydroxide). For the economic utilisation of the methodology for the manufacture of bulk single-enantiomer intermediates to, e.g. pharmaceuticals, it would be desirable to reduce the need for any excesses of reagents.

It has been discovered that, by the use of solutions of perborates, the amount of alkali, e.g. hydroxide, required in the reaction can be cut down substantially. As a result, apart from the saving in reagents, substrates may be used that are otherwise sensitive to the high alkali concentrations present. In the novel conditions, the oxidation system comprises the polymer, e.g. poly-amino-acid catalyst, an organic solvent such as dichloromethane, and an aqueous phase containing oxidant, e.g. (sodium) perborate, and alkali, e.g. sodium hydroxide. In addition, some phase transfer catalyst such as Aliquat 336 is added. A discovery is that not more than one equivalent of the alkali, e.g. sodium hydroxide, is required. These oxidation conditions may apply to other heterogeneous oxidations.

In addition, it has been found that a non-aqueous, two-phase oxidation protocol can be adopted, e.g. using the cheap, readily available oxidant urea hydrogen peroxide (UHP) in tert-butyl methyl ether containing diazabicycloundecane (DBU) with immobilised poly-(L)-leucine as the insoluble catalyst. There may be no need to pre-treat the polypeptide catalyst with aqueous organic solvent. Under these reaction conditions, the polymer appears as a paste rather than gel. The work-up of the reaction may be quite simple; the organic phase is decanted leaving the polymer in the reaction flask. The product is obtained from the organic phase after passage through a small pad of silica. The catalyst can be recycled at least six times without deterioration in the rate of the oxidation or the optical purity of the product.

Scheme 1 below illustrates reactions according to this invention, shows useful embodiments 1, 2 and 3, and an important, illustrative use of products of this invention. All these embodiments may be generalised to the scope of the invention.

The following Examples and Schemes 2 and 3 similarly illustrate the invention.

EXAMPLES 1 to 4

As shown in Table 1, a variety of epoxyketones ($R^2$+$R^3$=H) have been prepared in good to excellent yield and excellent optical purity (Example A is for comparison). All these epoxidations were carried out at ambient temperature in a three-phase system with an organic solvent, a catalytic amount of poly-L-leucine synthesised according to Flisak et al, J. Org. Chem. (1993) 58:6247, or poly-D-leucine synthesised in the same way from D-leucine, and with a large excess of oxidant. Preactivation of the catalyst, by stirring the mixture for 6 hours before addition of the α,β-unsaturated ketone, resulted in a shorter reaction time, e.g. of 1 to 3 days. Preferred solvents for these reactions are hydrocarbons such as hexane or chlorinated solvents such as dichloromethans. Optical purities (as given in Table 1) were as determined by HPLC on a Chiralpac AD column, and absolute configurations assigned as [2R,3S3] for those epoxides obtained from using poly-L-leucine. The catalyst could be recovered and reused.

TABLE 1

| Ex. | $R^1$ | X | Conditions | Yield (%) | ee (%) |
| --- | --- | --- | --- | --- | --- |
| A | Ph | isopropyl | (i) |  | 62 |
| 1 | Ph | t-butyl | (i) | 92 | >98 |
| 2 | Ph | t-butyl | (ii) | 90 | >86 |
| 3 | 2-naphthyl | cyclopropyl | (ii) | 61 | 90 |
| 4 | Ph—CH=CH— | cyclopropyl | (i) | 73 | 74 |

Conditions (i) = poly-L-leucine/$H_2O_2$/NaOH/$CHCl_2$
(ii) = poly-D-leucine/$H_2O_2$/NaOH/$CHCl_2$ The results summarised in Table 1 show that the epoxidation reaction has a broad substrate specificity and is therefore not restricted to chalcones. Satisfactory enantioselectivities were obtained, including a case where the substrate has a second conjugated double bond (Example 4). Example A was a relatively prolonged reaction, by comparison with Examples 1 and 2, owing to the possibility of enolisation.

Scheme 1

With reference to Scheme 1, as exemplification of the value of epoxyketones 1, a further aspect of the present invention is the use of (1S,2R)-1,2-epoxy-4,4-dimethyl-1-phenyl-3-pentanone 2 (synthon 3 is an alternative) in processes for the preparation of taxol side-chain synthons such as (2R,3S)-N-benzoyl-3-phenylisoserine synthons 4, wherein the t-butyl ketone functionality serves as a masked carboxylate. As summarised in Scheme 1, conversion of 2 to 4 can be accomplished by either of the following sequences:

(a) Baeyer-villiger oxidation to produce t-butyl 2,3-epoxy-3-phenylpropanoate 5, inversion of configuration at C-3 to afford cis-epoxide 6, nucleophilic ring opening at the benzylic position with either ammonia or azide anion (followed by reduction to the amine), N-benzoylation and optional acid-catalysed deesterification. In contrast to similar prior art processes for the corresponding n-alkyl ester (McChesney, Tetrahedron: Asymmetry (1994) 5:1683; Jacobsen, J. Org. Chem. (1992) 57:4320), during epoxide ring opening with ammonia the t-butyl ester provides effective protection against unwanted amidation at C-1, and allows final unmasking of the C-1 carboxyl group to be carried out under mild, non-hydrolytic conditions.

(b) Similar to (a), but with Baeyer-Villiger oxidation carried out at the penultimate stage. By this route the t-Bu ketone provides effective masking for the C-1 carboxyl group through much of the synthesis.

In Scheme 1, $R^1$ is H or acyl. The number of C atoms in the acyl group is not critical to the invention. An example is benzoyl. In the more general process shown in claim 26, $R^{11}$ is H or alkyl; again, the size of R is not critical.

Scheme 2

Scheme 2 shows another use for a compound of the invention, i.e. in the synthesis of an α-hydroxyester precursor to L-2-naphthylalanine.

Scheme 3

Scheme 3 shows a route to diltiazem. The two-phase oxidation (PLL, UHP, DBU) was applied to the ketone 13 which gave the epoxide 14 after 24 h (85% yield, >95% e.e.). This oxirane was subjected to a Baeyer-Villiger reaction (m-CPBA, KF) to furnish the ester 15. Subsequent reaction with o-aminothiophenyl and toluene reflux, followed hydrolysis of the ester (2 M NaOH, EtOH reflux), and lactam formation (p-T$_5$OH, xylene ref lux), afforded the alcohol 17. This alcohol is a well-documented precursor to diltiazem 18.

Scheme 1

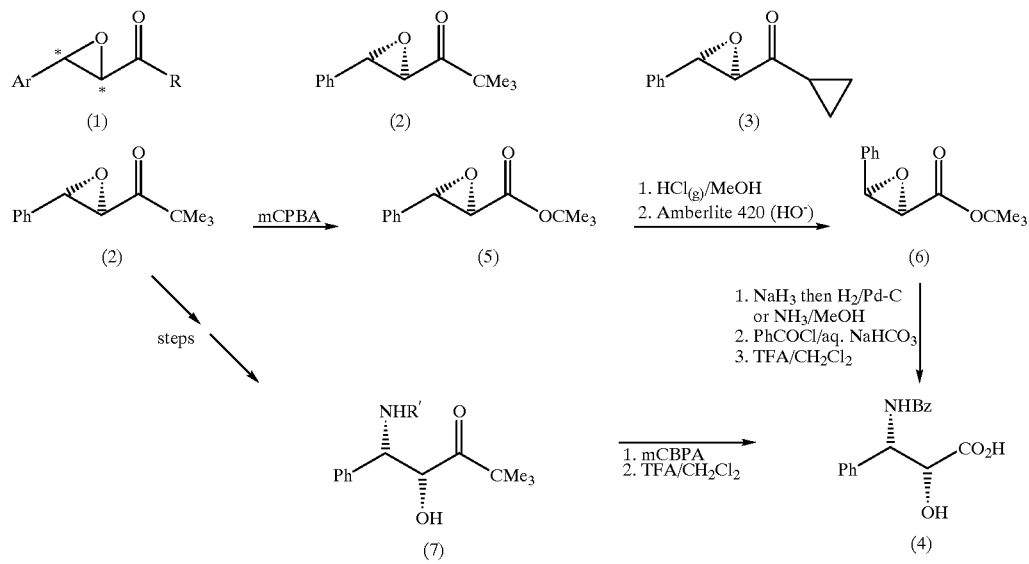

Scheme 2

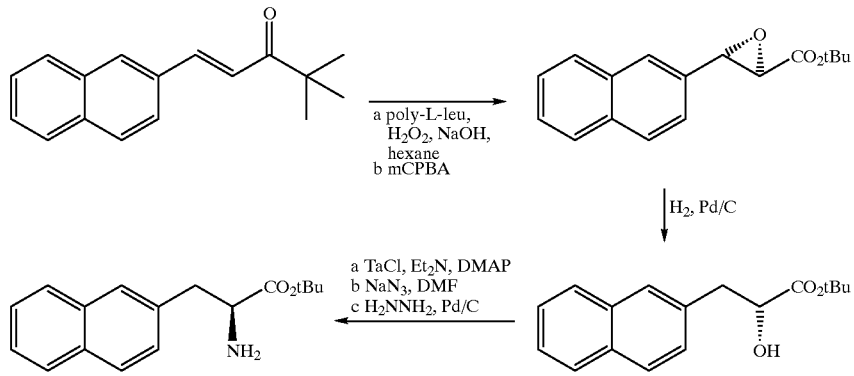

Scheme 3

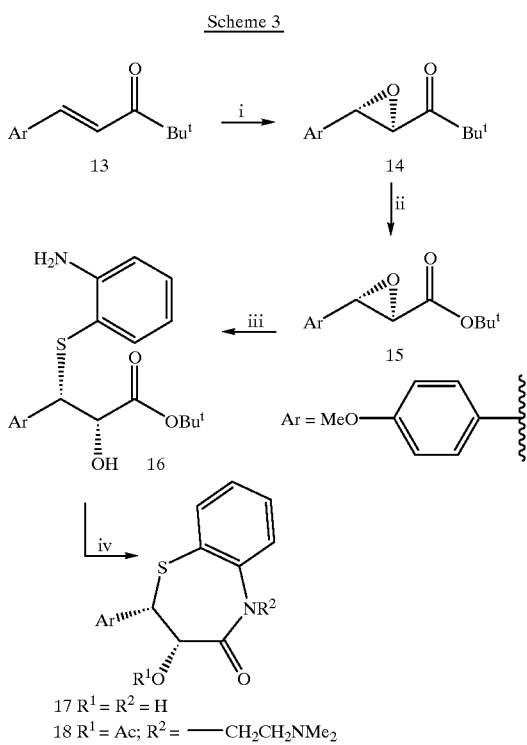

17 R¹ = R² = H
18 R¹ = Ac; R² = —CH₂CH₂NMe₂

We claim:

1. A process for preparing an enantiomerically enriched chiral epoxide of formula I

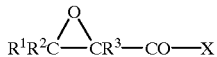  (I)

wherein $R^1$, $R^2$ and $R^3$ are each independently selected from H, R, R—CO— and R—O—CO—, each R independently being substantially a hydrocarbon group of up to 20 carbon atoms, and X is an alkyl or cycloalkyl group of up to 10 carbon atoms, provided that —CO—X is not enolisable, wherein said process comprises the asymmetric epoxidation of corresponding prochiral alkene of formula II $R^1R^2C=CR^3—CO—X$  (II)

by reaction with an oxidant in the presence of a chiral catalyst.

2. The process according to claim 1, wherein the catalyst is a heterogeneous chiral polymer.

3. The process according to claim 1, wherein the catalyst is a metal-free synthetic polypeptide.

4. The process according to claim 1, wherein the catalyst is obtained by nucleophile-promoted oligomerisation of an amino-acid carboxy anhydride.

5. The process according to claim 4, wherein the anhydride has the partial formula

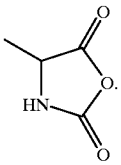

6. The process according to claim 5, wherein the oligomerisation is caused by humidity or an amine.

7. The process according to claim 1, which is conducted in the presence of alkali.

8. The process according to claim 7, wherein the alkali is hydroxide.

9. The process according to claim 2, which is conducted in a two- or three-phase mixture of the polymer, an organic solvent and, optionally, an aqueous phase, and containing the oxidant and, optionally, alkali.

10. The process according to claim 1, wherein $R^2$ and $R^3$ are each H.

11. The process according to claim 10, wherein $R^1$ is H.

12. The process according to claim 10, wherein $R^1$ is a group of up to 10 carbon atoms.

13. The process according to claim 12, wherein $R^1$ is 4-methoxyphenyl.

14. The process according to claim 1, wherein X is t-butyl.

15. The process according to claim 14, for the preparation of (1S, 2R)-trans-1,2-epoxy-4,4-dimethyl-1-phenyl-3-pentanone from (E)-4,4-dimethyl-1-phenylpenten-3-one.

16. The process according to claim 14, for the preparation of (1S, 2R)-trans-1,2-epoxy-1-(4-methoxyphenyl)-4,4-dimethyl-3-pentanone from (E)-1-(4-methoxyphenyl)-4,4-dimethyl-1-penten-3-one.

17. An enantiomerically enriched chiral epoxide of formula I as defined in claim 1, wherein $R^1$ is aryl or heteroaryl, optionally linked via a epoxide group to $CR^2$.

18. The epoxide according to claim 17, wherein $R^1$ is optionally-substituted phenyl.

19. The epoxide according to claim 18, wherein $R^1$ is 4-methoxyphenyl.

20. The epoxide according to claim 18, wherein $R^1$ is phenyl.

21. The epoxide according to claim 16, wherein X is t-alkyl.

22. The epoxide according to claim 17, wherein X is t-butyl or cyclopropyl.

23. The epoxide according to claim 17, which is in more than 80% enantiomeric excess.

24. A process for the preparation of an enamtiomerically enriched epoxide ester, wherein said process comprises converting X in an epoxide according to claim 17, to OX, by the Baeyer-Villiger reaction.

25. The process according to claim 24, wherein OX is t-butoxy.

* * * * *

UNITED STATES PATENT AND TRADEMARK OFFICE
CERTIFICATE OF CORRECTION

PATENT NO. : 6,228,955 B1  Page 1 of 1
DATED : May 8, 2001
INVENTOR(S) : Stanley Michael Roberts, Brian Michael Adger It is certified that error appears in the above-identified patent and that said Letters Patent is hereby corrected as shown below:

<u>Column 8,</u>
Line 50, "enamtiomerically" should read -- enantiomerically --.

Signed and Sealed this

Thirteenth Day of November, 2001

Attest:

*Nicholas P. Godici*

NICHOLAS P. GODICI
*Attesting Officer*   *Acting Director of the United States Patent and Trademark Office*